United States Patent
Diamond et al.

(10) Patent No.: US 7,442,386 B2
(45) Date of Patent: Oct. 28, 2008

(54) SYNTHESIS AND USE OF REAGENTS FOR IMPROVED DNA LIPOFECTION AND/OR SLOW RELEASE PRODRUG AND DRUG THERAPIES

(75) Inventors: Scott L. Diamond, Bala Cynwyd, PA (US); Jeffrey Alan Gruneich, Boston, MA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 104 days.

(21) Appl. No.: 10/777,805

(22) Filed: Feb. 12, 2004

(65) Prior Publication Data

US 2005/0069577 A1 Mar. 31, 2005

Related U.S. Application Data

(63) Continuation of application No. PCT/US02/26152, filed on Aug. 15, 2002.

(60) Provisional application No. 60/358,138, filed on Feb. 20, 2002, provisional application No. 60/312,729, filed on Aug. 16, 2001.

(51) Int. Cl.
*A61K 9/127* (2006.01)
*A61K 31/56* (2006.01)

(52) U.S. Cl. ..................... 424/450; 514/181
(58) Field of Classification Search ................. 514/181
See application file for complete search history.

(56) References Cited

U.S. PATENT DOCUMENTS

| | | | |
|---|---|---|---|
| 4,160,452 A | | 7/1979 | Theeuwes |
| 4,256,108 A | | 3/1981 | Theeuwes |
| 4,265,874 A | | 5/1981 | Bonsen |
| 5,650,096 A | * | 7/1997 | Harris et al. ............... 516/67 |
| 5,965,434 A | * | 10/1999 | Wolff et al. ............. 435/320.1 |
| 6,517,828 B1 | * | 2/2003 | Lin et al. ................... 424/93.2 |
| 6,696,038 B1 | * | 2/2004 | Mahato et al. ............. 424/1.45 |

OTHER PUBLICATIONS

Ashwell et al., "Glucocorticoids in T Cell Development and Function," *Ann. Rev. Immunol.* 18:209-345 (2000).
Braun et al., "In vitro and in vivo effects of glucocorticoids on gene transfer to skeletal muscle," *FEBS Letters* 454:277-282 (1999).
Galigniana et al., "Inhibition of Glucocorticoid Receptor Nucleocytoplasmic Shuttling by Okadaic Acid Requires Intact Cytoskeleton," *J. Biol. Chem.* 274:16222-16227 (1999).
Geall et al., "Synthesis of Cholesteryl Polyamine Carbamates: $pK_a$ Studies and Condensation of Calf Thymus DNA," *Bioconjugate Chem.* 11:314-326 (2000).
Lasic, "Liposomes," *Liposomes In Gene Delivery* Ch.6:67-113 (1997).
Li et al., "Effect of Immune response on gene transfer to the lung via systemic administration of cationic lipidic vectors," *J. Physiol.* 276:L796-L804 (1999).
McEwan et al., "Mechanism of gene expression by the glucocorticoid receptor: role of protein-protein interactions," *Bioessays* 19:153-160 (1997).
McNally et al., "The Glucocorticoid Receptor: Rapid Exchange with Regulatory Sites in Living Cells," *Science* 287:1262-1265 (2000).
Savory et al., "Discrimination between NL1- and NL2-Mediated Nuclear Localization of the Glucocorticoid Receptor," *Mol. Cell Biol.* 19:1025-1037 (1999).
Scheule et al., "Basis of Pulmonary Toxicity Associated with Cationic Lipid-Mediated Gene Transfer to the Mammalian Lung," *Human Gene Ther.* 8:689-707 (1997).
Simmons et al., "α-Keto Mesylate: A Reactive, Thiol-Specific Functional Group," *J. Org. Chem.* 45:3084-3088 (1980).
Streetz et al., "Mediators of Inflammation and Acute Phase Response in the Liver," *Cell Mol. Biol.* 47:661-673 (2001).
Subramanian et al., "Nuclear targeting peptide scaffolds for lipofection of nondividing mammalian cells," *Nat. Biotech.* 17:873-877 (1999).
Tan et al., "The Inhibitory Role of CpG Immunostimulatory Motifs in Cationic Lipid Vector-Mediated Transgene Expression in Vivo," *Hum. Gene Therapy* 10:2153-2161 (1999).
Tousignant et al., "Comprehensive Analysis of the Acute Toxicities Induced by Systemic Administration of Cationic Lipid: Plasmid DNA Complexes in Mice," *Hum. Gene Ther.* 11:2493-2513 (2000).
Walker et al., "Using Inducible Vectors to Study Intracellular Trafficking of GFP-Tagged Steroid/Nuclear Receptors in Living Cells," *Methods* 19:386-393 (1999).
Wiseman et al., "Steroid hormone enhancement of gene delivery to a human airway epithelial cell line in vitro and mouse airways in vivo," *Gene Therapy* 8:1562-1571 (2001).

* cited by examiner

*Primary Examiner*—Richard Schnizer
(74) *Attorney, Agent, or Firm*—Drinker Biddle & Reath LLP

(57) ABSTRACT

The invention relates to compositions and methods for a one-step synthetic technique for making cationic steroid or cationic drug molecules for use as delivery vehicles. The invention further relates to methods for using cationic steroid molecules in lipofection or transfection, delivery of drugs, and for treatment of inflammation and other diseases and disorders. The invention also relates to cationic steroid prodrugs and cationic prodrugs and to methods of modifying drugs.

5 Claims, 12 Drawing Sheets

FIG.3A
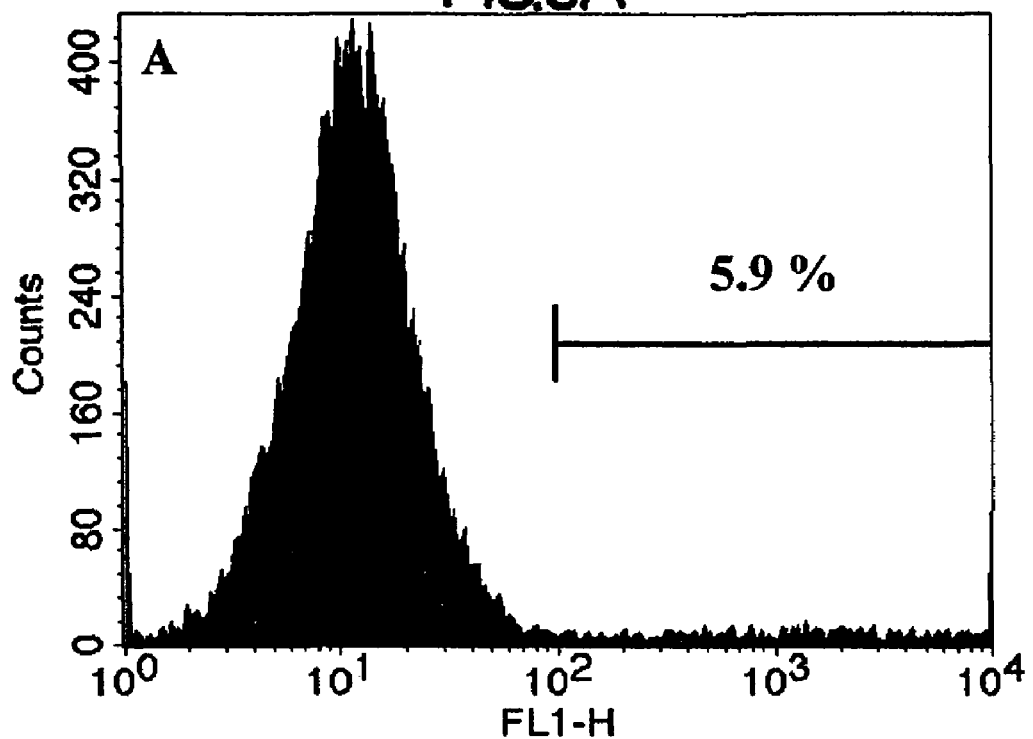
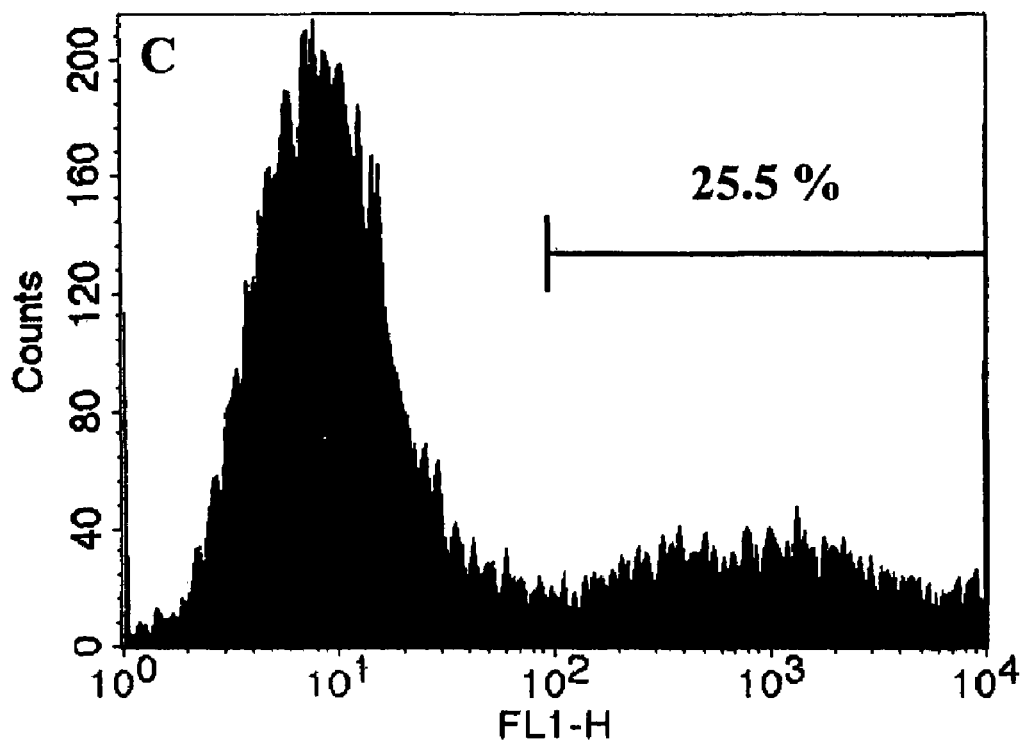
FIG.3C

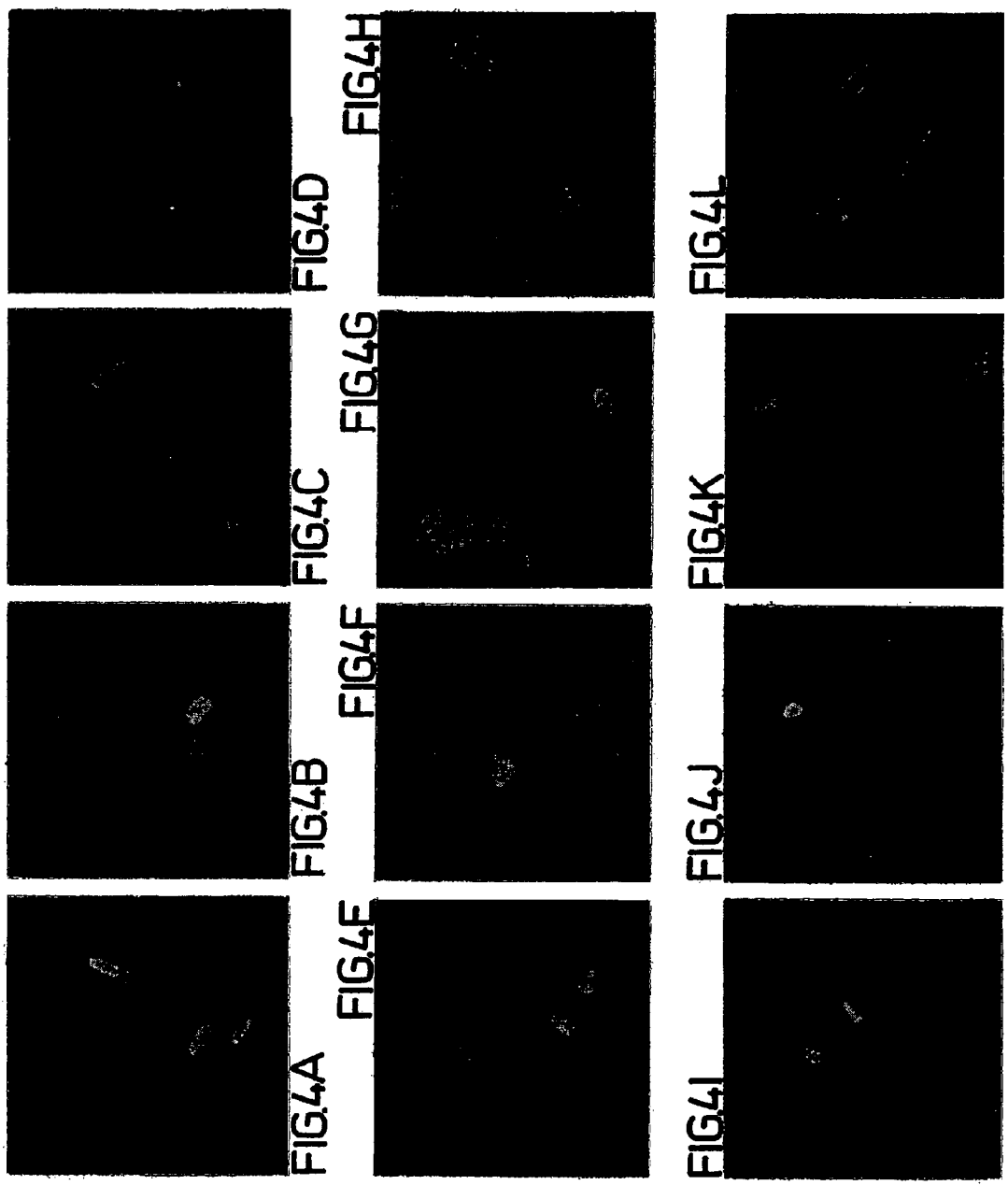

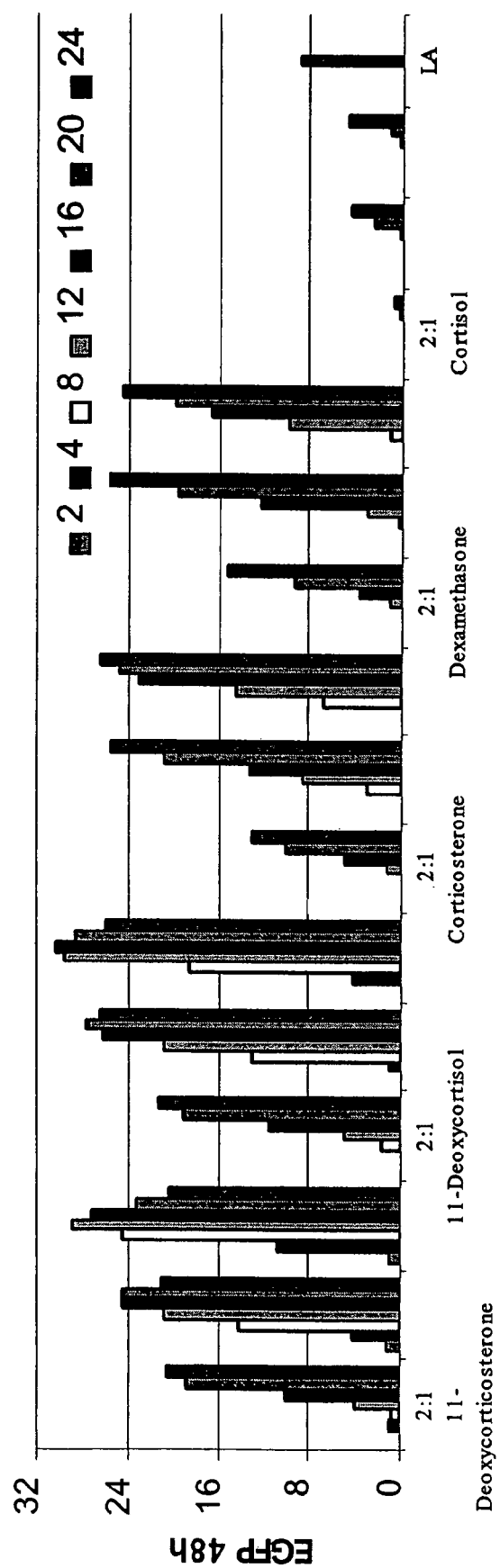

SYNTHESIS AND USE OF REAGENTS FOR IMPROVED DNA LIPOFECTION AND/OR SLOW RELEASE PRODRUG AND DRUG THERAPIES

CROSS REFERENCE TO RELATED APPLICATIONS

This Application is a continuation of International Application No. PCT/US02/26152, filed Aug. 15, 2002, which claims priority to U.S. Provisional Patent Applications No. 60/312,729, filed Aug. 16, 2001, and No. 60/358,138, filed Feb. 20, 2002.

BACKGROUND OF THE INVENTION

The immunological responses to unmethylated CpG motifs on plasmid DNA (Tan et al., 1999, Hum. Gene Ther. 10:2153-2161), cationic lipid formulations (Tousignant et al., 2000, Hum. Gene Ther. 11:2493-2513), and lipid/DNA lipoplexes (Tousignant et al., 2000, Hum. Gene Ther. 11:2493-2513; Scheule et al., 1997, Hum. Gene Ther. 8:689-7071; Li et al., 1999, Am. J. Physiol. 276:L796-L804) present major obstacles to nonviral gene delivery. Although transgene expression occurs within hours after plasmid delivery (Li et al. 1999, Am. J. Physiol. 276:L796-L804) the immunostimulatory cytokines TNF-α and IL-6 are also detected by one hour after systemic (Tousignant et al. 2000. Hum. Gene Ther. 11:2493-2513) or intranasal (Scheule et al. 1997, Hum. Gene Ther. 8:689-7071) administration. Other immunomodulatory cytokines, such as IFN-γ and IL-12, remain elevated for several days thereafter (Lasic, 1997, Liposomes in Gene Delivery, CRC Press). This rapid immune response to lipoplexes resembles the acute phase response to infection, which consists of local tissue reactions and systemic reactions by the liver, mediated chiefly by the inflammatory cytokine IL-6 (Streetz et al, 2001, Cell. Mol. Biol. 47:661-673). The inflammatory cytokines lead to an activation of endothelial cells and an influx of neutrophils, lymphocytes, and macrophages at the site of gene delivery (Tousignant et al. 2000, Hum. Gene Ther. 11:2493-2513; Scheule et al. 1997, Hum. Gene Ther. 8:689-7071). As a result, immunological responses to nonviral DNA delivery decrease the magnitude and duration of expression of the transgene and decrease the effectiveness of frequent dosing (Li et al. 1999, Am. J. Physiol. 276:L796-L804). Pharmacological doses of anti-inflammatory glucocorticoids prior or concurrent to administration of lipoplexes have a positive impact on inhibiting an immune response to a plasmid, resulting in an increased amount and duration of transgene expression, increased lifetime of plasmid, and shortened windows of time between dosing (Tan et al. 1999. Hum. Gene Ther. 10:2153-2161; Braun et al., 1999, FEBS Letters 454:277-282; Wiseman et al., 2001, Gene Ther. 8:1562-1571).

Glucocorticoids bind the glucocorticoid receptor (GR), inducing exposure of a classical nuclear localization sequence that allows importin $\alpha/\beta_1$ binding and subsequent trafficking into the nucleus (Galigniana et al., 1999, J. Biol. Chem. 274:16222-16227; Savory et al., 1999, Mol. Cell. Biol. 1025-1037). Glucocorticoids are also potent anti-inflammatory molecules that regulate the immune system by: (1) inhibiting the production or release of major cytokines such as IL-1, IL-6, TNF-α and IFN-γ; (2) decreasing the stability of mRNA encoding IL-1, IL-2, IL-6, IL-8, TNF-α, and GM-CSF; and (3) inhibiting cytokine-induced transcription by AP1 and NF-κB via the GR (Ashwell et al., 2000, Ann. Rev. Immunol. 18:209-345; McEwan et al., 1997, Bioessays 19:153-160; Schimmer et al., 1996, in The Pharmacological Basis of Therapeutics 1459-1485, McGraw-Hill). Liganded GR forms dimers that bind 15 base-pair glucocorticoid response elements (GREs) to induce or repress transcription (Schimmer et al., 1996, in The Pharmacological Basis of Therapeutics 1459-1485, McGraw-Hill; McNally et al., 2000, Science 287:1262-1265).

Viral and non-viral vectors are used as the basis for gene delivery in current nucleic acid and gene therapy methods. However, there are concerns about the production, reproducibility, cost, and safety of viral vectors for gene therapy. As a result, work has focused on the development of nonviral vectors where the gene construct of interest is packaged by synthetic nonviral materials. Examples of such materials include polycations, dendrimers, and polysaccharides, as well as small molecule cationic lipids such as dioleylphosphatidylethanolamine (DOPE), 3-beta-[N',N' dimethylaminoethane)-carbamoyl]cholesterol (DC-chol), and spermine cholesterol. For example, cationic lipids for lipofection condense plasmids, facilitate endosome escape, neutralize charge of DNA, and/or shield DNA from nucleases (Lasic, 1997, Liposomes in Gene Delivery, CRC Press).

There is a long felt need in the art for the development of new compositions and methods for nucleic acid delivery which produce high levels of transfection and for drug delivery which produce high levels of incorporation into a cell, and which also includes the ability to deliver drugs locally. There is also a need for such a delivery platform which has inherent pharmacological or biological activity and increased pharmacokinetic half-life and sustained depot action. The present invention satisfies these needs.

SUMMARY OF THE INVENTION

The invention generally relates to compositions and methods for a one-step synthetic technique for making cationic steroid or cationic drug molecules for use as delivery vehicles. The invention further relates to methods for using cationic steroid molecules in lipofection or transfection, delivery of drugs, and for treatment of inflammation and other diseases and disorders. The invention also relates to cationic steroid prodrugs and cationic prodrugs.

In one embodiment, the invention relates to a method of making a cationic nonviral delivery vehicle comprising mixing together a steroid or a drug or a modification or derivative thereof, a conjugating reagent, and a polyamine, wherein said conjugating reagent conjugates said steroid or drug or a modification or derivative thereof with said polyamine, purifying the newly formed conjugated steroid-polyamine molecule or conjugated drug-polyamine molecule, and mixing the conjugated steroid-polyamine molecule or drug-polyamine molecule with a lipid.

In one aspect of the invention, dimethylsulfoxide is mixed with the steroid or drug or a modification or derivative thereof, said conjugating reagent, and said polyamine.

In one embodiment of the invention, the invention also relates to methods for modifying existing drugs to create new drug entities with new pharmacokinetic/pharmacodynamic properties. In one aspect of the invention, the new drug entity may or may not be used with a lipid. In another aspect of the invention, the new drug entity may function on its own or as a pro-drug that releases an active drug.

In one embodiment, the steroid is selected from the group consisting of a glucocorticoid, a mineralcorticoid, an androgen, an estrogen, a progestagen, an analog with steroidal agonist activity, an analog with steroidal antagonist activity, an inactive structural analog, and modifications or derivatives thereof. In one aspect, the steroid is selected from the group consisting of a cationic steroid and a cationic steroid prodrug.

In one embodiment, the cationic nonviral delivery vehicle binds with an anionic domain of a molecule selected from the group consisting of a glycosaminoglycan, a collagen, a fibrin, a cellular glycocalyx, a red blood cell glycocalyx, a sialic acid, a sulfated glycocalyx, and an isolated nucleic acid. In one aspect, the glycosaminoglycan is hyaluronic acid.

In one aspect of the invention, the steroid is selected from the group consisting of dexamethasone, 11-deoxycorticosterone-21-mesylate, corticosterone-21-mesylate, 11-dexoxycortisol-21-mesylate, cortisol-21-mesylate, tamoxifen, 4-hydroxy tamoxifen, 21-chloro-17hydroxyprogesterone, cholesterol tosylate, hydrocortisone mesylate, 17 α-mesylate-estradiol-3-acetate, and dexamethosone-21-mesylate.

In another aspect of the invention, the conjugating reagent is 2-iminothiolane.

In one embodiment of the invention, the polyamine is selected from the group consisting of spermine, a polylysine, lysine, a lysine containing peptide, an arginine containing peptide, a cationic polymer, and an amine rich polymer. In one aspect of the invention, the polymer is polyethyleneimine (PEI).

In a further embodiment of the invention, the lipid is a neutral lipid. In one aspect of the invention, the lipid is a helper lipid. In another aspect of the invention, the neutral lipid is selected from the group consisting of dioleylphosphatidylethanolamine (DOPE) and cholesterol. In yet another aspect of the invention, the lipid is a cationic lipid.

The invention further relates to a drug of the delivery vehicle which is a hydrophobic drug. In aspect the drug is a mesylate derivative. In another aspect of the invention the drug is selected from the group consisting of a cationic drug and a cationic prodrug.

The invention also relates to a kit for administering a cationic nonviral delivery vehicle of the invention.

The invention further relates to a method for facilitating delivery of a compound to a cell, interstitial space, or tissue, comprising administering a composition comprising the compound and an effective amount of a cationic nonviral delivery vehicle of the invention. In one aspect of the invention the delivery vehicle comprises a steroid and in another aspect it comprises a drug. In another aspect, the compound binds an anionic constituent of the interstitial space or tissue, allowing it to be slowly released from the delivery vehicle. In yet another aspect of the invention, the delivery vehicle binds an anionic constituent of the interstitial space or tissue, allowing the compound to be slowly released from the delivery vehicle.

In one embodiment of the invention, the compound delivered by the delivery vehicle is a nucleic acid, a drug or a modification or derivative thereof, or another molecule.

In one embodiment of the invention the delivery vehicle delivers a compound to a cell of an animal. In one aspect of the invention, the cell is a mammalian cell, and in another aspect the cell is a human cell.

The invention also relates to a method of treating a disease or disorder in a mammal, comprising administering to the mammal a composition comprising a cationic nonviral delivery vehicle and an effective amount of a compound. In one aspect of the invention, the delivery vehicle comprises a steroid and in another it comprises a drug. The invention also relates to a method of treating a disease of disorder by treating with additional compounds, which may or may not be administered with a delivery vehicle of the invention. The invention further relates to kits for treating a disease or disorder in a mammal.

The invention includes a method for facilitating incorporation of a compound into a cell, using a delivery vehicle of the invention. In one aspect of the invention the delivery vehicle comprises a steroid and in another it comprises a drug.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings. In the drawings:

FIG. 2, comprising In FIG. 2A, lipofections of 1 μg of plasmid per well (2-cm$^2$/well at ~4×10$^5$ cells/well) for expression of enhanced green fluorescent protein (EGFP) were carried out at increasing amounts of total lipid (0 to 40 μg) per μg DNA and various DS:DOPE mass ratios of 1:0 μg/μg DS:DOPE (light gray); 2:1 μg/μg DS:DOPE (dark gray); 1:1 μg/μg DS:DOPE (gray); 1:2 μg/μg DS:DOPE (off-white); 0:1 μg/μg DS:DOPE (white); as well as for Lipofectamine at 6 μg lipid: 1 μg DNA when neither DS nor DOPE was present (black). FIG. 2B demonstrates optimization of the lipid:DNA ratio at 1:2 g/μg DS:DOPE by optimizing the expression of EGFP as a function of charge ratio to DNA, and led to 10-fold enhancement of EGFP production relative to Lipofectamine. EGFP expression was normalized to the expression obtained with Lipofectamine. GFP positive BAEC imaged by epifluorescence microscopy were lipofected with Lipofectamine (FIG. 2C), unconjugated dexamethasone/spermine/DOPE (FIG. 2D), or DS/DOPE (E). The results indicate that dexamethasone must be conjugated to spermine to have transfer or delivery activity.

FIG. 3, comprising FIGS. 3A-3D, illustrates a FACS analysis and images of a microscopic analysis of lipofections using Lipofectamine or DS/DOPE. Confluent BAEC cells were lipofected with 6:1 Lipofectamine:DNA (A, B) or 6:12:1 DS:DOPE:DNA. (C, D) and subjected to flow cytometry (A, C) or epifluorescence microscopy (B, D). FACS analysis showed a 4.3-fold increase in percent transfection using DS/DOPE versus Lipofectamine, consistent with the increased transfection observed by direct visualization of EGFP in attached living cells.

FIG. 4, comprising FIGS. 4A through 4M, illustrates that cationic steroids are pharmacologically active. FIGS. 4A through 4L are images of photomicrographs showing that a 30 minute treatment of 3T3 cells expressing GFP-GR protein with dexamethasone, DS/DOPE, or the hydrolysis product DA caused nuclear localization of GFP-GR at doses of 1000 nM (first column), 100 nM (second column), and 10 nM (third column). Untreated cells (fourth column—FIGS. 4D, 4H, and 4L) displayed predominantly cytosolic localization of the fluorescent glucocorticoid receptor protein (0 nM). Dexamethasone (lower panel) and DA (upper panel) induced nuclear localization at 10 nM concentrations, while DS/DOPE (middle panel) had slightly less activity at this dose. FIG. 4M demonstrates that dexamethasone, the cationic steroid DS, and its hydrolysis product DA, all caused dose-dependent induction of SEAP transcription from a GRE-SEAP reporter plasmid as indicated by a fluorogenic assay for secreted alkaline phosphatase activity. Promoter construct experiments were made in triplicate, $**p<0.001$; $*p<0.005$, $+p<0.05$.

DETAILED DESCRIPTION

General Description

Figure 1A:
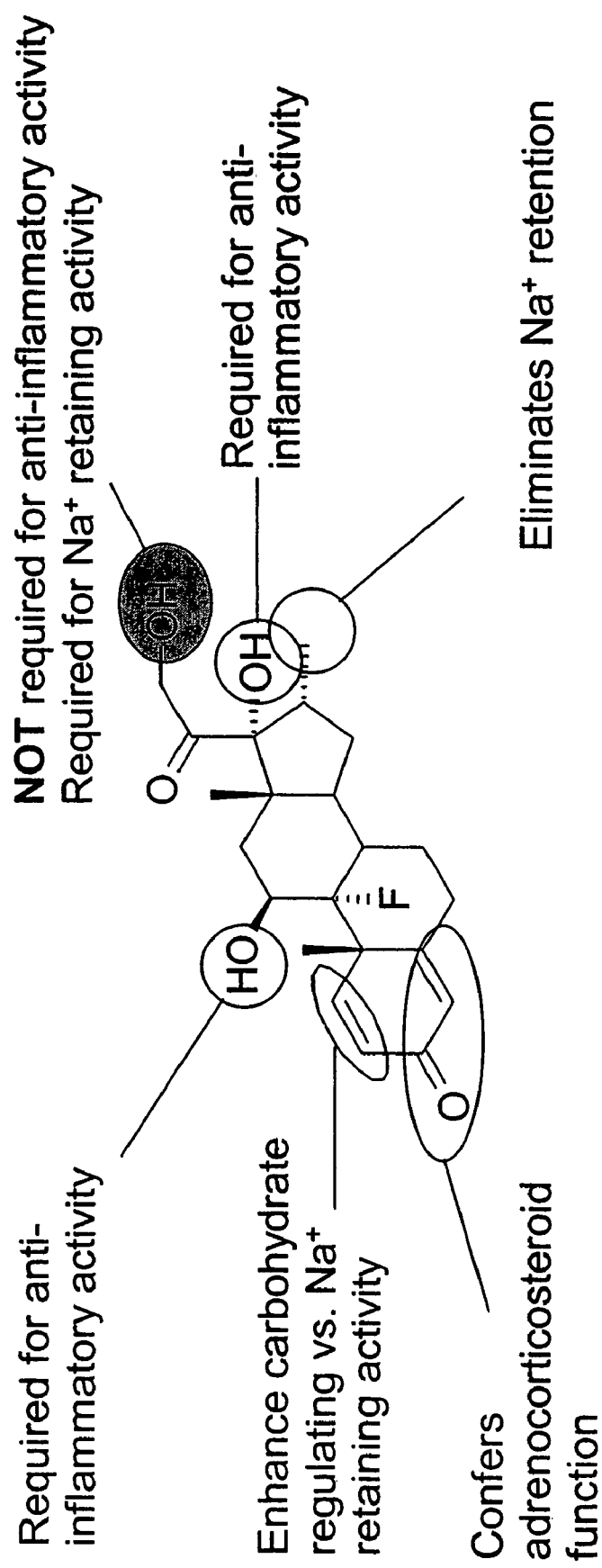
FIG. 1, comprising FIGS. 1A and 1B, schematically illustrates synthesis of a cationic steroid for nucleic acid or drug delivery and anti-inflammatory activity. The 21-hydroxy position of dexamethasone was chosen for conjugation of a cationic group since it can be substituted without loss of glucocorticoid function (FIG. 1A).
In FIG. 1B it can be seen that the use of 2-iminothiolane (Traut's reagent) as a coupling reagent does not consume a cation on spermine during the synthesis of the cationic steroid, dexamethasone-spermine (DS; Product 1). Under basic conditions, the prodrug DS undergoes hydrolysis, releasing spermine and a dexamethasone-amide (DA; Product 2).

The invention relates generally to compositions and methods for making and using a nonviral delivery vehicle for delivering molecules such as nucleic acids or drugs to cells, both in vivo and in vitro. The invention relates specifically to a nonviral delivery vehicle comprising a cationic lipid nonviral delivery vehicle, said vehicle comprising a steroid or other hydrophobic pharmaceutical agent or drug conjugated to a polyamine and used in conjunction with a lipid. The invention also relates to modifying existing drugs to create new drug entities with new pharmacokinetic/pharmacodynamic properties. The methods of the invention include making the delivery vehicle and use of the delivery vehicle. The invention also relates to use of the delivery vehicle to transfect nucleic acids into cells. The invention further relates to a platform chemistry or delivery vehicle with inherent pharmacological or biological activity, such as anti-inflammatory activity that offers new pharmacokinetic or pharmacodynamic properties distinct from the parent pharmaceutical agent or compound, and that can be used alone or with other agents.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, "alleviating a disease or disorder symptom," means reducing the severity of the symptom.

A "cationic lipid" or "cationic steroid" or "cationic drug" is a lipid or steroid or drug or hydrophobic moiety which has a positive charge, or is part of a complex which has a positive charge, such as a steroid coupled with a polyamine.

A "compound," as used herein, refers to any type of substance or agent that is commonly considered a drug, or a candidate for use as a drug, as well as combinations and mixtures of the above.

The term "delivery vehicle", as used herein, refers to a molecule or composition useful for binding or carrying another molecule, such as a nucleic acid or drug, and delivering it to a target site, such as a cell. "Delivery vehicle" is used interchangeably with terms such as "drug delivery vehicle" "nucleic acid delivery vehicle", or "delivery vector".

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, are reduced.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains.

An "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, the term "fragment", as applied to a protein or peptide, can ordinarily be at least about 3-15 amino acids in length, at least about 15-25 amino acids, at least about 25-50 amino acids in length, at least about 50-75 amino acids in length, at least about 75-100 amino acids in length, and greater than 100 amino acids in length. As used herein, the term "fragment", as applied to a nucleic acid, can ordinarily be at least about 20 nucleotides in length, typically, at least about 50 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 350, even more preferably, at least about 350 nucleotides to about 500 nucleotides, yet even more preferably, at least about 500 to about 600, even more preferably, at least about 600 nucleotides to about 620 nucleotides, yet even more preferably, at least about 620 to about 650, and most preferably, the nucleic acid fragment will be greater than about 650 nucleotides in length.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g, as a cDNA or a genomic or cDNA fragment produced by PCR or restriction enzyme digestion) independent of other sequences. It also includes a recombinant DNA which is part of a hybrid gene encoding additional polypeptide sequence.

The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

The term "peptide" typically refers to short polypeptides.

As used herein, the term "pharmaceutically-acceptable carrier" means a chemical composition with which an appropriate delivery vehicle and nucleic acid, drug, or compound can be combined and which, following the combination, can be used to administer the appropriate delivery vehicle and nucleic acid, drug, or compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Polyamine" as used herein refers to polymers of amines as well as to other types of molecules containing amines, such as amine rich polymers or other amine containing polymers, a lysine containing peptide, and an arginine containing peptide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

A "polynucleotide" means a single strand or parallel and anti-parallel strands of a nucleic acid. Thus, a polynucleotide may be either a single-stranded or a double-stranded nucleic acid.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but can be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

A "prophylactic" treatment is a treatment administered to a subject who does not exhibit signs of a disease or exhibits only early signs of the disease for the purpose of decreasing the risk of developing pathology associated with the disease.

The term "protein" typically refers to large polypeptides.

"Slow release," as used herein, refers to delivery of a nucleic acid, drug, or molecule to a cell, tissue, or organ, wherein the nucleic acid, drug, or molecule is not all readily available because some remains bound to the delivery vehicle or to an anionic molecule and is slowly released for availability over a period of time. The period of time should be at least 10% longer than availability that is not slow release, preferably at least 25% longer, more preferably at least 35% longer, and even more preferably at least 50% longer. Such a drug or molecule can include a prodrug or steroid prodrug.

"Synthetic peptides or polypeptides" mean a non-naturally occurring peptide or polypeptide. Synthetic peptides or polypeptides can be synthesized, for example, using an automated polypeptide synthesizer. Those of skill in the art know of various solid phase peptide synthesis methods.

A "therapeutic" treatment is a treatment administered to a subject who exhibits signs of pathology, for the purpose of diminishing or eliminating those signs.

"Tissue", as used herein, refers to the general definition of tissue which includes a collection of similar cells and the intercellular substances and spaces surrounding them, and the term is also used herein to include collections of similar cells in tissues and organs.

The term "topical application", as used herein, refers to administration to a surface, such as the skin. This term is used interchangeably with "cutaneous application".

By "transdermal" delivery is intended both transdermal (or "percutaneous") and transmucosal administration, i.e., delivery by passage of a drug through the skin or mucosal tissue and into the bloodstream. Transdermal also refers to the skin as a portal for the administration of drugs or compounds by topical application of the drug or compound thereto.

The term to "treat," as used herein, means reducing the frequency with which symptoms are experienced by a patient or subject or administering an agent or compound to reduce the frequency with which symptoms are experienced.

As used herein, "treating a disease or disorder" means reducing the frequency with which a symptom of the disease or disorder is experienced by a patient. Disease and disorder are used interchangeably herein.

A "vector", as used herein, refers to either a delivery vehicle as described herein or to a vector such as an expression vector.

Synthesis and Hydrolysis of Cationic Steroids or Drugs for Use as Nucleic Acid and Drug Delivery Vehicles It has been discovered in the present invention that using novel methods steroids or drugs can be conjugated with a polyamine, and that the resultant molecule can bind nucleic acids, drugs, and other molecules (See Examples 1-4). The invention further encompasses methods for making steroids, drugs, or other compounds or molecules cationic. Furthermore, it has been discovered in the present invention that when coupled with a lipid, this nonviral molecule is capable of delivering nucleic acids and drugs to cells (Examples 1 and 2). It has also been discovered in the present invention that the steroid can maintain its inherent biological activity once coupled with the polyamine. It has been discovered in the invention that various steroids, polyamines, and lipids are useful for the methods of the invention. In addition, it is disclosed herein that the delivery vehicle of the present invention has the ability to target molecules of interstitial spaces as potential delivery sites to allow slow release of a compound at a local interstitial site. Interstitial space or tissue includes extracellular space. The invention also includes methods of using the invention to treat a disease and kits to administer the nonviral delivery vehicle.

The invention also relates to methods for modifying existing drugs to create new drug entities with new pharmacokinetic/pharmacodynamic properties using the platform chemistry of the invention. The new drug entity may or may not be used with a lipid. The new drug entity may function on its own or as a pro-drug that releases an active drug.

The present invention discloses novel methods for delivering nucleic acids, including DNA, to cells and causing transfection of said DNA into a cell and expression of the DNA.

The invention should be construed to include various steroids or hydrophobic drugs as described herein, including glucocorticoids, and should not be construed to include only the steroids described herein. Such steroids included, but are not limited to, a mineralcorticoid, an androgen, an estrogen, a progestagen, an analog with steroidal agonist activity, an analog with steroidal antagonist activity, an inactive structural analog, and modifications or derivatives thereof. For example, additional steroids which are useful in the invention include, cortexolone mesylate, cortisone mesylate, prednisone 21-mesylate, 3β-iodocholesterol, 16β-bromo-4-androsten-3,17-dione, 2α-bromo-5α-cholestan-3-one, 16α-bromoestradiol, 16α-bromoestrone, 16β-bromoestrone, 17α-bromopregnenolone, 17-bromoprogesterone, androsterone tosylate, cholestanol tosylate, cholesteryl tosylate, dehydroepiandrosterone tosylate, dihydrotestosterone tosylate, epiandrosterone tosylate, 11α-hydroxyprogesterone tosylate, 19-nortestosterone tosylate, pregnenolone tosylate, and testosterone tosylate. The invention should be construed to include active and inactive analogs, modifications, and derivatives of the steroids and drugs, as well as steroid prodrugs and prodrugs.

In addition, the invention should be construed to include various polyamines, including spermine. In addition to the polyamine spermine, the invention should be construed to include any polyamine, including, but not limited to, spermidine, polylysine, proteins, peptides, oligonucleotides, other biopolymers, synthetic polyamines, such as polyimines (for example, polyethyleneimine), a lysine containing peptide, an arginine containing peptide, a cationic polymer, and an amine rich polymer, and amino dendrimers.

In one aspect of the invention the lipid is a cationic lipid and in another aspect the lipid is a neutral lipid. Neutral lipids of the invention include, but are not limited to, DOPE, phosphatidylcholine (PC), and cholesterol. Cationic lipids of the invention include, but are not limited to, 3-beta-[N',N'dimethylaminoethane)-carbamoyl]cholesterol) (DC-Chol), N[1-(2,3-dioleyloxy)propyl [N,N,N-triethyl-ammonium (DOTMA), 2'-(1",2"-dioleoyloxypropyldimethyl-ammonium bromide)-N-ethyl-6-aminospermine tetra trifluoroacetic acid (DOSPA), 1,3-bis(oleoyloxy)-3-(trimethylammonio)propane (DOTAP), and GL-67. In one aspect of the invention, the lipid is a helper lipid to aid in delivery of a nucleic acid, drug, or other compound. Furthermore, the invention should be construed to include lipids other than those described herein.

In one embodiment of the invention a steroid or drug and a polyamine such as spermine are coupled using a coupling reagent. In one aspect of the invention the reagent is 2-iminothiolane. In another aspect of the invention, a steroid or drug and spermine are also mixed with dimethylsulfoxide. In yet another aspect of the invention, a purified steroid-polyamine complex or purified drug-polyamine complex are mixed with a lipid to form a delivery vehicle.

In Vitro Molecule Delivery with a Cationic Lipid Nonviral Delivery Vehicle

Various methods and assays have been described herein to synthesize a steroid-polyamine complex or a drug-polyamine complex of the invention and methods to add lipids to the complex to arrive at a cationic lipid nonviral delivery vehicle of the present invention. Various assays have also been disclosed herein to demonstrate the ability of the delivery vehicle to bind a compound and to deliver a compound to a cell. Preferably the cell is a mammalian cell, and more preferably the cell is a human cell.

The invention includes methods of treating a disease or disorder in a mammal, using a nonviral delivery vehicle of the invention. In one aspect of the invention the vehicle delivers a nucleic acid and in another aspect the vehicle delivers a drug or another compound. In one aspect the mammal is a human. Diseases or disorders of the invention which may be treated using a delivery vehicle of the invention include, but are not limited to, inflammation, asthma, arthritis, pain, inflammation of joints, cancer, allergies, hypertension, neoplasia, hyperplasia, metastasis, claudication, intimal hyperplasia, hemophilia, anemia, coagulopathies, autoimmune disorders, duodenal ulcers, gastric ulcers, erosive esophagitis, pathological hypersecretory conditions, rhinitis, chronic idiopathic urticaria, hypersecretory conditions, heartburn, candidiasis, Helicobacter pylori infection, osteoarthritis, rheumatoid arthritis, familial adenomatous polyposis, depression, obsessive-compulsive disorder, bulimia nervosa, premenstrual dysphoric disorder, psychotic disorders, bipolar disorder, obsessive-compulsive disorder, posttraumatic stress disorder, panic disorder, panic disorder, social anxiety disorder, schizophrenia, psychotic disorders, generalized anxiety disorder, dysmenorrhea, menopausal symptoms, osteoporosis, prostate cancer, breast cancer, hypoestrogenism, Kraurosis vulvae, hypercholesterolemia, congestive heart failure, cardiac ischemic complications, myocardial infarction, hypertension, left ventricular dysfunction, type 2 diabetes, ovarian cancer, nonsmall cell lung cancer, Kaposi sarcoma, hairy cell leukemia, warts, malignant melanoma, hepatitis C, hepatitis B, non-Hodgkin lymphoma, erectile dysfunction, epilepsy, Paget disease, neutropenia, progenitor cell mobilization, heart transplant rejection, kidney transplant rejection, liver transplant rejection, psoriasis, pain, cluster headache, migraine, angina, gastritis, endometriosis, central precocious puberty, bronchospasm, gastro-esophageal reflux disease, mastocytosis, and proliferative disorders.

Some examples of diseases which may be treated according to the methods of the invention are described above. The invention should not be construed as being limited solely to these examples, as other diseases or disorders which are at present unknown, once known, may also be treatable using the methods of the invention In one embodiment of the invention, the delivery vehicle delivers a nucleic acid, steroid, drug, or compound to a cell. In one aspect of the invention the cell is selected from the group consisting of an endothelial cell, a mesenchymal cell, a neural cell, a fibroblast, neuron, a smooth muscle cell, a kidney cell, a liver cell, a myoblast, a stem cell, an embryonic stem cell, a hematopoietic stem cell, an osteoblast, a chondrocyte, a chondroblast, a monocyte, a neutrophil, a macrophage, a retinal nerve cell, and an epithelial cell. Preferably the cell is a mammalian cell. More preferably it is a human cell.

In one embodiment of the invention, the delivery vehicle delivers a nucleic acid, steroid, drug, or compound to a tissue. In one aspect of the invention, the tissue comprises muscle, mucosa, epithelial, nerve, connective, blood, stromal, heart, liver, kidney, skin, brain, intestinal, interstitial space, bone, bone marrow, joint, cartilage, tendon, esophagus, gonad, cerebrospinal fluid, pancreas, spleen, ocular, nasal cavity, and hair tissue.

The invention should not be construed as being limited solely to these examples, as other diseases and disorders treatable by the nonviral delivery vehicle of the invention which are at present unknown, once known, may also be treatable using the methods of the invention.

In one embodiment of the invention, a disease or disorder is treated by administering the delivery vehicle and a nucleic acid or drug via an oral route. Other routes of administration, include, but are not limited to intranasal, rectal, vaginal, intramuscular, topical, subdermal, sublingual, intraperitoneal, and intravenous.

The invention relates to the administration of a nonviral delivery vector and an identified nucleic acid, drug, or other molecule to be delivered, in a pharmaceutical composition to practice the methods of the invention. The composition comprises the nonviral delivery vector and an identified nucleic acid, drug, or other molecule to be delivered and a pharmaceutically-acceptable carrier. For example, a nonviral delivery vehicle with which an appropriate identified nucleic acid, drug, or other molecule to be delivered, is combined, is used to administer an identified nucleic acid, drug, or other molecule to be delivered an animal. One of skill in the art would recognize that when more than one nucleic acid or drug or other compound is being administered, each additional one may be delivered with a delivery vehicle of the invention and/or additional nucleic acids, drugs, or other molecules may be delivered independent of a delivery vehicle of the invention.

The invention should not be construed to being limited solely to the isolated nucleic acids, drugs, or other molecules described herein as those which may be delivered by a delivery vehicle of the invention. The invention should be construed to include other nucleic acids, drugs or other molecules not described herein, which can also be delivered by the delivery vehicle of the invention. These other nucleic acids, drugs, or other molecules with which the delivery vehicle of the invention can bind and/or deliver include, but are not limited to, hydrophobic chemical entities, fat soluble drugs, anionic chemical entities, anionic radionucleotides, anionic or hydrophobic radioisotopes for chemotherapy, oligonucleotides, single or double stranded RNA or DNA oligonucleotides or nucleotides or fragments thereof, PCR products, RNA-DNA chimeric molecules, RNAi (RNA interference), peptide-nucleic acid (PNA), peptides or proteins containing anionic acid groups such as glutamic or aspartic acid, heparin, low molecular weight heparin, anionic glycosaminoglycans, anionic or hydrophobic fluorescent molecules, and viral particles or subfractions of virus particles. Other molecules and drugs which are included among the compounds which can be delivered by the delivery vehicle of the invention include, but are not limited to, recombinant proteins, erythropoietin, tissue plasminogen activator (tPA), tumor necrosis factor-alpha receptor, Omeprazole, Simvastatin, Atorvastatin calcium, Amlodipine besylate, Loratadine, Lansoprazole, Epoetin alfa, Celecoxib, Fluoxetine hydrochloride, Olanzapine, Paroxetine hydrochloride, Rofecoxib, Sertraline hydrochloride, Epoetin alfa, a conjugated estrogens, Amoxicillin and clavulanate Potassium, Pravastatin sodium, Enalapril maleate, Metformin hydrochloride, Pravastatin, Losartan potassium, Ciprofloxacin hydrochloride, Risperidone, Paclitaxel, Azithromycin, interferon alpha-2b, rebavirin, Sildenafil citrate, Gabapentin, Fluticasone propionate, Alendronate sodium, Clarithromycin, Filgrastim, cyclosporine, Lisinopril dihydrate, venlafaxine HCl, human insulin, Levofloxacin, Fexofenadine, Hydrochloride, Lisinopril/lisinopril, Sumatriptan succinate, Nifedipine, Fluconazole, Ceftriaxone sodium, Famotidine, Enoxaparin sodium, Leuprolide acetate, Salmeterol xinafoate, Clopidogrel bisulfate, Lansoprazole, and Ranitidine. The delivery vehicle of the invention may also bind with anionic domains in polymers such as an anionic glycosaminoglycan, a collagen, a fibrin, a cellular glycocalyx, a red blood cell glycocalyx, a sialic acid, a sulfated glycocalyx, a deoxyribonucleic acid and a ribonucleic acid.

The invention further relates to the used of cationic steroid prodrugs and cationic prodrugs and slow release therapies. In one embodiment of the invention, the delivery vehicle or the nucleic acid, drug, compound, or molecule being delivered by the delivery vehicle may target molecules of interstitial and extracellular spaces by binding to said molecules. Such binding then allows slow release of the nucleic acid, drug, compound, or molecule at a local site.

In one embodiment, the pharmaceutical compositions useful for practicing the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 100 g/kg/day.

Pharmaceutically acceptable carriers which are useful include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Pharmaceutical compositions that are useful in the methods of the invention may be administered, prepared, packaged, and/or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

The compositions of the invention may be administered via numerous routes, including, but not limited to, oral, rectal, vaginal, parenteral, topical, pulmonary, intranasal, buccal, or ophthalmic administration routes. The route(s) of administration will be readily apparent to the skilled artisan and will depend upon any number of factors including the type and severity of the disease being treated, the type and age of the veterinary or human patient being treated, and the like.

Pharmaceutical compositions that are useful in the methods of the invention may be administered systemically in oral solid formulations, ophthalmic, suppository, aerosol, topical or other similar formulations. In addition to the compound such as heparan sulfate, or a biological equivalent thereof, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer compounds according to the methods of the invention.

Compounds which are identified using any of the methods described herein may be formulated and administered to a mammal for treatment of various diseases, disorders, or conditions described herein.

The invention encompasses the preparation and use of pharmaceutical compositions comprising a compound useful for treatment of various diseases, disorders, or conditions described herein. Such a pharmaceutical composition may consist of the active ingredient alone, in a form suitable for administration to a subject, or the pharmaceutical composition may comprise at least one active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limits the penetration rate (flux) of a compound through the stratum corneum is the amount of the active substance which can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts.

Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

The source of active compound to be formulated will generally depend upon the particular form of the compound. Small organic molecules and peptidyl or oligo fragments can be chemically synthesized and provided in a pure form suitable for pharmaceutical/cosmetic usage. Products of natural extracts can be purified according to techniques known in the art. Recombinant sources of compounds are also available to those of ordinary skill in the art.

In alternative embodiments, the topically active pharmaceutical or cosmetic composition may be optionally combined with other ingredients such as moisturizers, cosmetic adjuvants, anti-oxidants, chelating agents, bleaching agents, tyrosinase inhibitors and other known depigmentation agents, surfactants, foaming agents, conditioners, humectants, wetting agents, emulsifying agents, fragrances, viscosifiers, buffering agents, preservatives, sunscreens and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art. The compositions of this invention may also contain active amounts of retinoids (i.e., compounds that bind to any members of the family of retinoid receptors), including, for example, tretinoin, retinol, esters of tretinoin and/or retinol and the like.

The topically active pharmaceutical or cosmetic composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compounds may be synthetically- or naturally-derived.

Liquid derivatives and natural extracts made directly from biological sources may be employed in the compositions of this invention in a concentration (w/v) from about 1 to about 99%. Fractions of natural extracts and protease inhibitors may have a different preferred rage, from about 0.01% to about 20% and, more preferably, from about 1% to about 10% of the composition. Of course, mixtures of the active agents of this invention may be combined and used together in the same formulation, or in serial applications of different formulations.

The composition of the invention may comprise a preservative from about 0.005% to 2.0% by total weight of the composition. The preservative is used to prevent spoilage in the case of an aqueous gel because of repeated patient use when it is exposed to contaminants in the environment from, for example, exposure to air or the patient's skin, including contact with the fingers used for applying a composition of the invention such as a therapeutic gel or cream. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating agent which inhibit the degradation of the compound for use in the invention in the aqueous gel formulation. Preferred antioxidants for some compounds are BHT, BHA, alphatocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefor as would be known to those skilled in the art.

Controlled-release preparations may also be used and the methods for the use of such preparations are known to those of skill in the art.

In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gelcaps, and caplets, that are adapted for controlled-release are encompassed by the present invention.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, microspheres or a combination thereof that facilitates the controlled-release of the active ingredient.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

As used herein, an "oily" liquid is one which comprises a carbon-containing liquid molecule and which exhibits a less polar character than water.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, a paste, a gel, a toothpaste, a mouthwash, a coating, an oral rinse, or an emulsion. The terms oral rinse and mouthwash are used interchangeably herein.

A pharmaceutical composition of the invention may be prepared, packaged, or sold in a formulation suitable for oral or buccal administration. Such a formulation may comprise, but is not limited to, a gel, a liquid, a suspension, a paste, a toothpaste, a mouthwash or oral rinse, and a coating. For example, an oral rinse of the invention may comprise a compound of the invention at about 1.4%, chlorhexidine gluconate (0.12%), ethanol (11.2%), sodium saccharin (0.15%), FD&C Blue No. 1 (0.001%), peppermint oil (0.5%), glycerine (10.0%), Tween 60 (0.3%), and water to 100%. In another embodiment, a toothpaste of the invention may comprise a compound of the invention at about 5.5%, sorbitol, 70% in water (25.0%), sodium saccharin (0.15%), sodium lauryl sulfate (1.75%), carbopol 934, 6% dispersion in (15%), oil of spearmint (1.0%), sodium hydroxide, 50% in water (0.76%), dibasic calcium phosphate dihydrate (45%), and water to 100%. The examples of formulations described herein are not exhaustive and it is understood that the invention includes additional modifications of these and other formulations not described herein, but which are known to those of skill in the art.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject.

Douche preparations may further comprise various additional ingredients including, but not limited to, antioxidants, antibiotics, antifungal agents, and preservatives. As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

Typically, dosages of the compound of the invention which may be administered to an animal, preferably a human, will vary depending upon any number of factors, including but not limited to, the type of animal and type of disease state being treated, the age of the animal and the route of administration.

The compound can be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the disease being treated, the type and age of the animal, etc.

It will be recognized by one of skill in the art that the various embodiments of the invention as described above relating to methods of treating diseases, disorders or conditions, includes other diseases, disorders and conditions not described herein.

The invention further includes kits for treating a disease or disorder in an animal.

In accordance with the present invention, as described above or as discussed in the Examples below, there can be employed conventional chemical, cellular, histochemical, biochemical, molecular biology, microbiology and recombinant DNA techniques which are known to those of skill in the art. Such techniques are explained fully in the literature. See for example, Sambrook et al., 1989 Molecular Cloning—a Laboratory Manual, Cold Spring Harbor Press; Glover, (1985) DNA Cloning: a Practical Approach; Gait, (1984) Oligonucleotide Synthesis; Harlow et al., 1988 Antibodies—a Laboratory Manual, Cold Spring Harbor Press; Roe et al., 1996 DNA Isolation and Sequencing: Essential Techniques, John Wiley; and Ausubel et al., 1995 Current Protocols in Molecular Biology, Greene Publishing.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Synthesis and Hydrolysis of Cationic Steroids

There is a need in the art to be able to easily synthesize vectors or vehicles useful for nonviral delivery of molecules to and into cells. A method to fulfill this need is disclosed in the present invention.

The Materials and Methods used in the present example are now described.

Synthesis of Cationic Steroids

Dexamethasone mesylate or dexamethasone (Steraloids, NH), 2-iminothiolane (Traut's reagent) (Pierce), spermine (Sigma), and DMSO (Aldrich) were used as received. A total of 105 mg (223 µmol) of dexamethasone-mesylate, 800 µl of DMSO, and 28.4 mg (206 µmol) of Traut's reagent were dissolved together prior to addition of 31.9 µl (145 µmol) of spermine at room temperature. After 45 min, the reaction was complete by TLC. HPLC purification (60/40 0.1% TFA/acetonitrile, Hamilton PRP-1 column) and freeze-drying yielded DS as a white powder. Yield: 15.3 mg (14.0%).

Large Scale, High Yield, Multi-Gram Synthesis of Steroid Mesylate Precursor for Conjugation A 200 ml Erlenmeyer flask equipped with a magnetic stir bar and a rubber septum was charged with 5 grams of dexamethasone (12.7 mmol, 1 equivalent) and 16 ml of anhydrous pyridine. The flask was cooled to 0° C. with an ice bath, and 1.2 ml of methanesulfonyl chloride was added. After 1 hour, 0.8 ml of additional methanesulfonyl chloride was added. At two hours, the solution was poured into 100 ml of cold 1M HCl, forming a precipitate. The precipitate was filtered and redissolved in 250 ml of ethanol, and precipitated into 250 ml of 1M HCl. The precipitate was filtered and recrystallized in ethanol, filtered, and dried under vacuum yielding 4.95 g (82.6%) of dexamethasone mesylate.

Large Scale, Multi-Gram, High Yield Synthesis of N-[3-({4-[(3-aminopropyl)amino]butyl}amino)propyl]-4-[(9-fluoro-11,17-dihydroxy-16-methyl-3,20-dioxopregna-1,4-dien-21-yl)sulfanyl]butanimidamide-TFA salt (1,Dexamethasone-Spermine, DS)

A 1-L round-bottom flask equipped with a magnetic stir bar and rubber septum was purged with nitrogen and charged with 600 ml of USP-grade dry ethanol, 60 ml of anhydrous THF, 4.95 grams (10.5 mmol, 1.05 equivalents) of dexamethasone-mesylate and 10 grams (19.5 mmol, 4.95 equivalents) of spermine. 2-Iminothiolane, 1.38 grams (10 mmol, 1.0 equivalents) in 3 ml of water, was added dropwise to the solution over 5 minutes with vigorous mixing. The solution changed color from clear to clear light yellow. The reaction was monitored by TLC and by analytical HPLC. After three hours at room temperature, the TLC spot at $R_f=0$ (the charged DS) ($R_f=0.7$ min DS by analytical HPLC) was maximized, and dexamethasone-mesylate ($R_f$ 0.47, 2.8 min HPLC) spot minimized. The crude reaction mixture was diluted with 15.25 ml (198 mmol, 19.8 equivalents) of trifluoroacetic acid, forming a white precipitate (spermine tetra TFA salt). Solvent was removed with a rotary evaporator and 50 ml of ethanol was added, forming a white precipitate (spermine-4TFA). The pH 3 solution was filtered twice to remove spermine tetratrifluoroacetic acid salt, and ethanol was removed with a rotary evaporator. 50 ml of water was added to the yellow viscous oil, yielding a precipitate (dexamethasone and dexamethasone mesylate), and the solution was filtered through 0.2 μm filter to yield a clear yellow liquid. Water was removed with a lyophilizer over several days to yield dexamethasone-spermine tetratrifluoroacetic acid salt. Yield: 8.228 grams (7.17 mmol, 72%).

TLC $R_f=0$, 50/50 Hexane/THF, analytical HPLC $R_f=0.7$ min. $^1$H NMR (500 MHz, DMSO) δ=6.23 (d, J=0.023, 1 H, C2), 6.01 (s, 1 H, C4), 5.33 (d, J=0.01, 1 H, C17-OH), 5.04 (s, 1 H, C11-OH), 4.14 (d, J=0.02, 1 H, C11-OH), 3.63 (dd, J=0.39, 0.03,2 H, C21), 3.37 (s, 20 H, Spermine), 3.27 (s, 2 H, Spermine), 3.93 (s, 4 H, Spermine), 2.61 (m, 1 H, C6a), 2.37 (m, 1 H, C6b), 2.33 (m, 1 H, C8), 2.17 (d, J=0.02, 1 H, C12), 2.1 (q, J=0.02, 1 H,C14), 1.87 (m, 4 H, Spermine), 1.78 (m, J=0.01, 1 H, C7a), 1.63 (m, 2 H, Spermine), 1.58 (m, 1 H, C15a), 1.48 (s, 3 H, C19), 1.46 (s, 1 H, C7), 1.07 (m, 1 H, C15b), 0.87 (s, 3 H, C18), 0.78 (d, 3 H, C22); HRMS (FAB$^+$) $C_{38}H_{63}FN_5O4S$: [M+H]$^+$ calcd 678.4428. found 678.4429.

Other methods which were used but not described herein are well known and within the competence of one of ordinary skill in the art of chemistry, immunology, and cellular and molecular biology.

The Results of the experiments described in this example are now presented.

Synthesis of Cationic Dexamethasone Prodrug

Figure 1B:
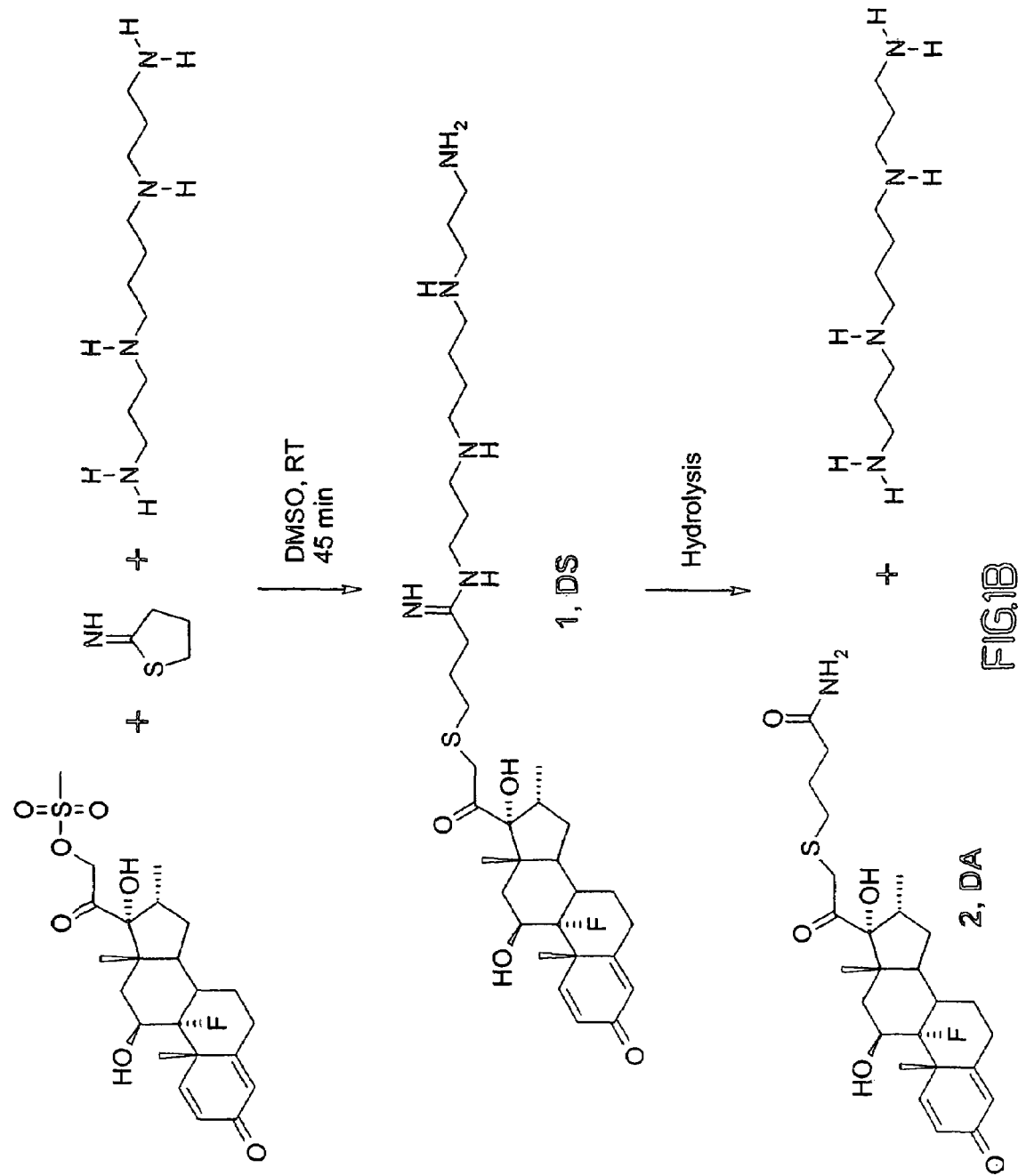

The 21-hydroxy group of dexamethasone is not required for anti-inflammatory activity, and therefore is an ideal choice for conjugation to a polycation (FIG. 1A) (Schimmer et al., 1996, in The Pharmacological Basis of Therapeutics, 1459-1485, eds. Hardman and Limbird, McGraw-Hill, New York). A one-pot reaction between spermine, 2-iminothiolane (Traut's reagent) and dexamethasone mesylate yielded the dexamethasone-spermine conjugate, (DS), as the major product (FIG. 1B). Traut's reagent is selectively ring-opened by the primary amines (Hermanson, 1996, Bioconjugate Techniques, Academic Press) on spermine, forming a hydrolytically sensitive amidimide bond (Hermanson, 1996, Bioconjugate Techniques, Academic Press) between spermine and iminothiolane and a reactive thiolate anion that reacts with the α-keto mesylate on the 21 position of dexamethasone mesylate (Simmons et al., 1980, J. Org. Chem. 45:084-3088), yielding an α-keto thioether linkage between the dexamethasone and iminothiolane. The conjugation reaction was complete in 45 minutes by TLC. $^1$H NMR of DS confirmed the presence of the 3-bis-enone and 11- and 17-hydroxy groups required for glucocorticoid activity (FIG. 1A) as well as $^1$H signals from the conjugated spermine and the 21-α-keto thioether group. Hydrolysis of DS in 1M NaOH for 20 minutes resulted in the cleavage of the amidimide linkage between spermine and iminothiolane, forming a dexamethasone-amide (DA) (FIG. 1B), which has a 21-substituted butyl thioether amide side-chain on dexamethasone. For DA, FIG. 1B: Calc: C: 63.26; H: 7.35; N: 2.84. Found: C: 63.44; H: 7.27; N: 2.83. Water solubility: DS>100,000 mg/l; DA 60 mg/l; (dexamethasone 100 mg/l).

There is a need in the art for a nonviral cationic lipid delivery vehicle which can deliver such molecules as nucleic acids or drugs to cells, interstitial sites, organs, or tissues. This invention satisfies this need.

Example 2

Molecule Delivery In Vitro with a Nonviral Cationic Steroid Delivery Vehicle

The Materials and Methods used in the present example are now described.

Cell Culture and Lipofection

Bovine aortic endothelial cells (BAEC, passage 4-13) were passaged at a 1:3 split to 24-well culture plates, and then grown to dense confluence before lipofection. Growth medium was Dulbecco's modified Eagle's medium (DMEM) containing 10% heat inactivated charcoal-filtered (to remove steroid hormones) fetal calf serum (Hyclone), 0.30 mg/ml glutamine, 150 U/ml penicillin, and 0.15 mg/ml streptomycin (Gibco). 293 cells were grown under identical conditions. The plasmids pEGFP-N3 and pGRE-SEAP (Clontech) were used for expression of EGFP or secreted alkaline phosphatase under the regulation of CMV or GRE promoters, respectively. Lipofectamine reagent (Gibco) containing 2:1 (μg:μg) mixture of polycationic lipid 2,3-dioleyloxy-N-[2(sperminecarboxamido)ethyl]-N,N-dimethyl-1-propanaminium trifluoroacetate (DOSPA):DOPE was used according to manufacturer's instructions.

Preparation and Characterization of Lipid Assemblies and Lipoplexes

To form the DS:DOPE lipid solution, 67 µl of a 10 mg/ml solution of DS in ethanol and 27 µl of a 50 mg/ml solution of DOPE in ethanol were vortexed together. After solvent evaporation with a $N_2$ stream, 1 ml of sterile Millipore water was added to the lipid film and the solution was sonicated for 10 min. The solution (2 µg of lipid per µl of water) was stored at 4° C. and retained lipofection activity for over 6 months (data not shown). The hydrodynamic diameter of DS/DOPE (1 µg/2 µg) obtained by dynamic light scattering (DynaPro 99 instrument) was 70 to 150 nm without DNA, while lipoplexes with 1 µg DNA and 0 to 20 equivalents of DS and 0 to 20 equivalents of DOPE had sizes ranging from 200 to 500 nm.

Fluorescence GFP Measurement

For lipofection, a solution of DS/DOPE in 125 µl Opti-MEM I (Gibco) was mixed with a solution of DNA in 125 µl OptiMEM I, incubated for 30 to 60 minutes, and then overlaid on BAEC cells for 2 hours, followed by PBS rinse and addition of growth media. Fluorescence was measured after 48 hours. At lipid concentrations exceeding charge ratios of 6:1 DS:DNA, the formulations began to display cytotoxicity in BAEC as indicated by altered morphology. EGFP expression of transfections was monitored in duplicate (FIG. 2A) or triplicate (FIG. 2B) with a fluorescent plate reader (Labsystems Fluoroskan Ascent; 485 nm/538 nm filter pair) with background subtraction using the autofluorescence of non-transfected BAEC. EGFP expression was calibrated using 0 to 200 ng recombinant GFP (Clontech) in 750 µl PBS. In assays of EGFP in lysates, lipofected cells were trypsinized, pelleted (200×g, 8 minutes), resuspended in 150 µl PBS, and subjected to 3× freeze/thaw at –78° C. The lysate was centrifuged at 13,500 RPM (5 minutes) in an Eppendorf Minifuge. Supernatant was collected, and pooled with supernatant from PBS washed and pelleted cells (total volume 750 µl), and EGFP fluorescence was measured (Ex 485, Em 515; SLM fluorometer). In separate experiments, flow cytometry of lipofected and trypsinized cells expressing EGFP was performed at the University of Pennsylvania Flow Cytometry Core Facility using a FACSCalibur instrument.

The Results of the experiments described in this example are now presented.

In vitro Gene Delivery with Cationic Steroids

Figure 2B:
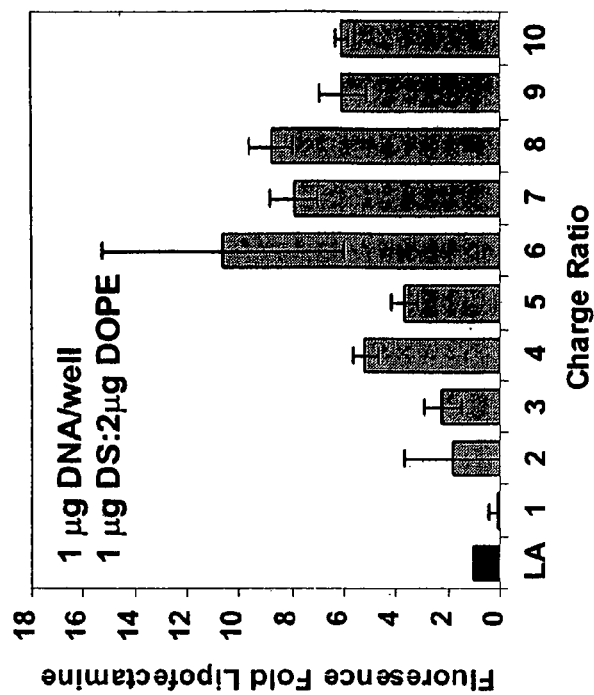
FIGS. 2A-2E, illustrates the optimization of cationic steroid lipoplex formulation for transfection of confluent bovine aortic endothelial cells.
Figure 2A:
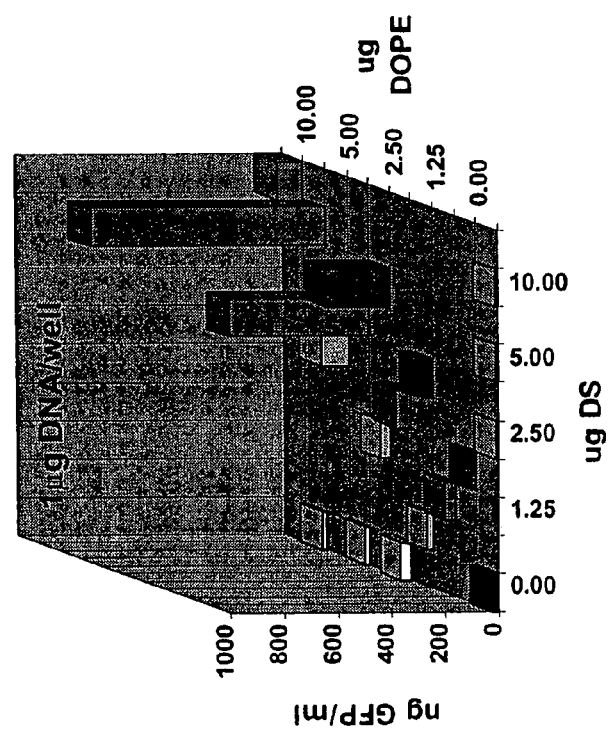
Figure 2E:
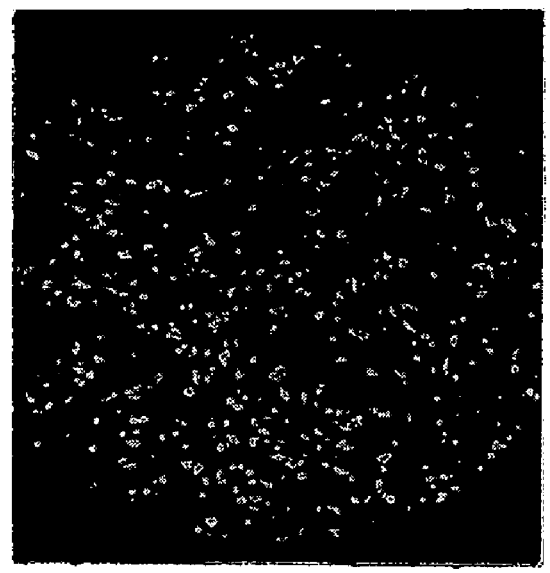
Figure 2D:
Figure 2C:
Figure 3B:
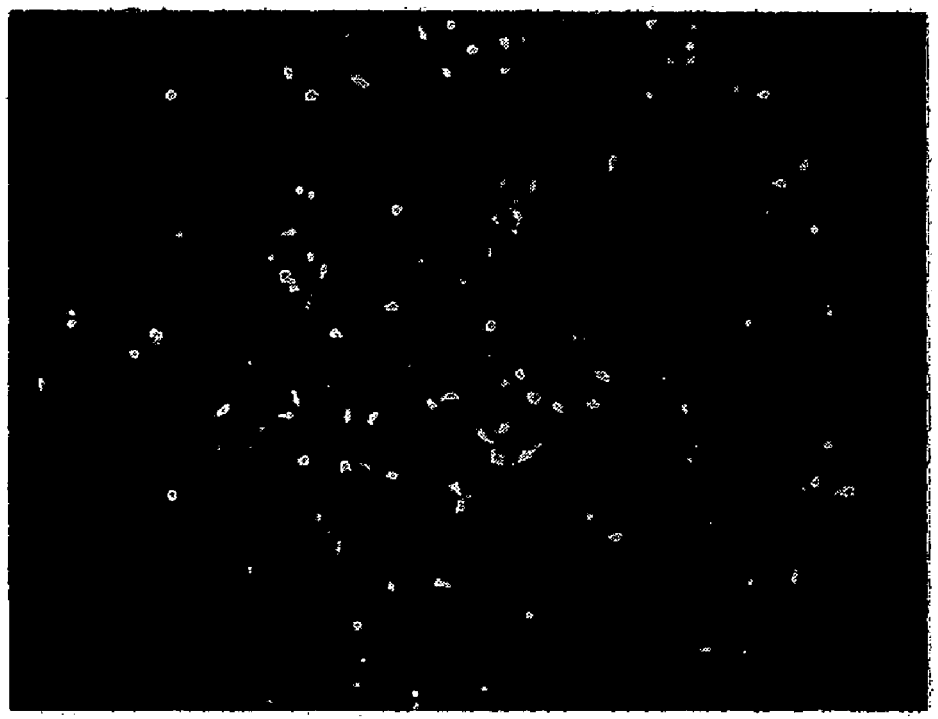
Figure 3D:
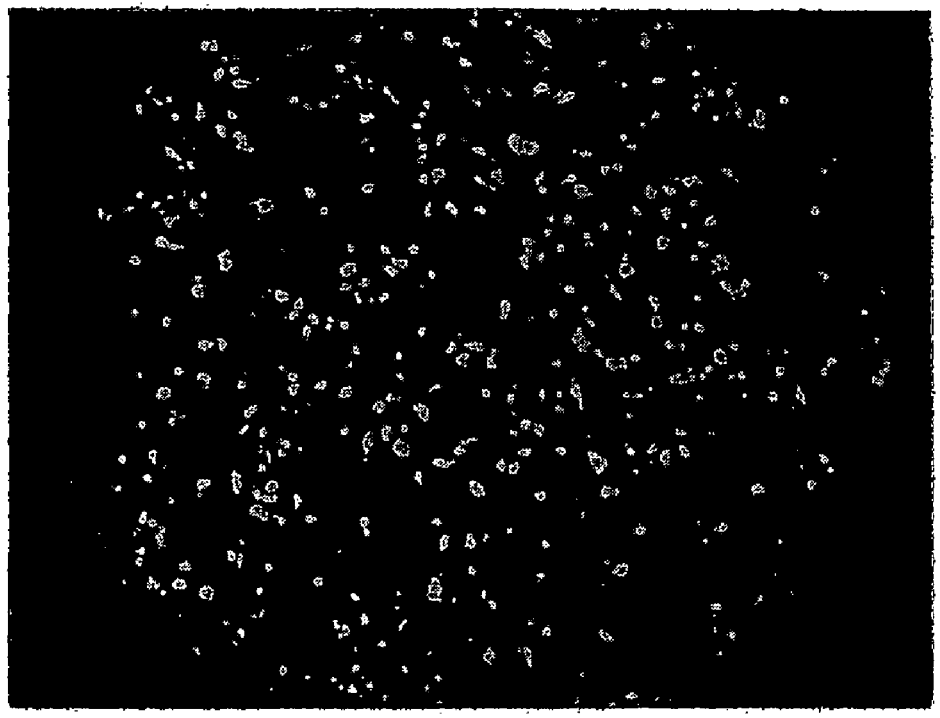

Using the neutral lipid dioleylphosphatidylethanolamine (DOPE) and 1 µg plasmid/well, we measured gene expression obtained with varying amounts of DS (0 to 20 µg) and varying amounts of DOPE (0 to 20 µg) (FIG. 2A). In the case where neither DS nor DOPE was present, Lipofectamine was used (6 µg/µg-DNA) as a benchmark. The mass ratio of 1:2 of DS:DOPE (light bars, FIG. 2A) provided high EGFP expression while minimizing the use of the DS conjugate and minimizing the total lipid load below 10 µg total lipid/µg DNA. In a separate set of experiments maintaining the DS:DOPE mass ratio constant at 1:2, the amount of DS relative to DNA was systematically varied from 1 to 10 charge equivalents (0.9 to 9 µg DS per µg DNA), assuming an average charge of the spermine of DS to be 3.8 per molecule (Geall et al., 2000, Bioconjug. Chem. 11:314-326) and no net charge contribution from DOPE. The optimal lipofection plateaued at a charge ratio of 6 DS:1 DNA, giving more than 10-fold increase in the amount of transgene expression relative to Lipofectamine reagent. Increases beyond a charge ratio of 6:1 DS:DNA provided no increase in expression (FIG. 2B). To test if gene transfer activity of DS was merely associated with the DNA binding ability of spermine and the hydrophobic character of dexamethasone, DNA was combined with spermine, dexamethasone, and DOPE (all unconjugated) using the same molar ratios and concentrations as in the conjugated DS/DOPE transfection (FIG. 2D). Only when the dexamethasone was conjugated with spermine was EGFP expression detected (FIG. 2E). Spermine alone or dexamethasone alone had no detectable gene transfer activity. Using a flow cytometry cutoff of 100 F.I. to define percent transfection (Subramanian et al., 1999, Nat. Biotech. 17:873-877), a 4.3-fold increase was observed in percent transfection over Lipofectamine from 5.9% to 25.5% (FIG. 3). Lipofection of subconfluent (proliferating) BAEC with DS/DOPE yielded a 4.6-fold increase in percent transfection over Lipofectamine from 16.0% with Lipofectamine to 73.8% lipofection with DS/DOPE (data not shown). Although hydrolysis of DS to DA is accelerated in 1M NaOH, the amidimide bond in DS appeared relatively stable in neutral pH when formulated with DOPE, since DS/DOPE formulations stored for six months at 4° C. in water retained their lipofection activity.

Synthesis and Use of Other Cationic Steroids in Delivery Vehicles

The conjugation of spermine to steroids was carried out to create molecules useful for DNA transfer to mammalian cells. 21-chloro-17hydroxyprogesterone, cholesterol tosylate, hydrocortisone mesylate, or 17 α-mesylate-estradiol-3-acetate was mixed with DMSO and Traut's reagent followed by addition of spermine. The resulting cationic steroids displayed gene transfer activity when used with the neutral lipid, DOPE, on 293 cells.

Figure 6A:
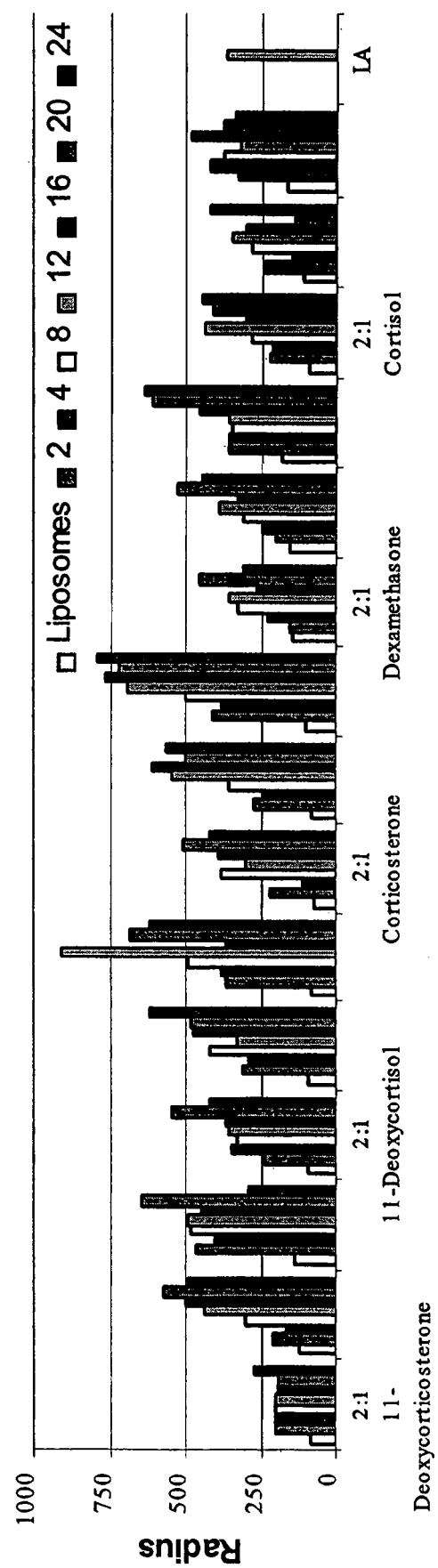
FIG. 6, comprising FIGS. 6A, 6B, and 6C, graphically illustrates structure and activity of a series of steroid-spermine conjugates and lipofectamine (LA) for DNA packaging and transfection in bovine aortic endothelial cells (BAEC). Dynamic light scattering (FIG. 6A) is given for steroid-spermines of varying Log Psteroid (Log Psteroid=1.6 to 2.9) at DOPE:steroid ratios of 0.5, 1, and 2 and amine:phosphate ratios ranging from 2 to 24. EGFP expression at 24 hours (FIG. 6B) and 48 hours (FIG. 6C) is given for each formulation tested in FIG. 6A. LogP is defined as the log of the octanol/water partitioning ratio.
Figure 6B:
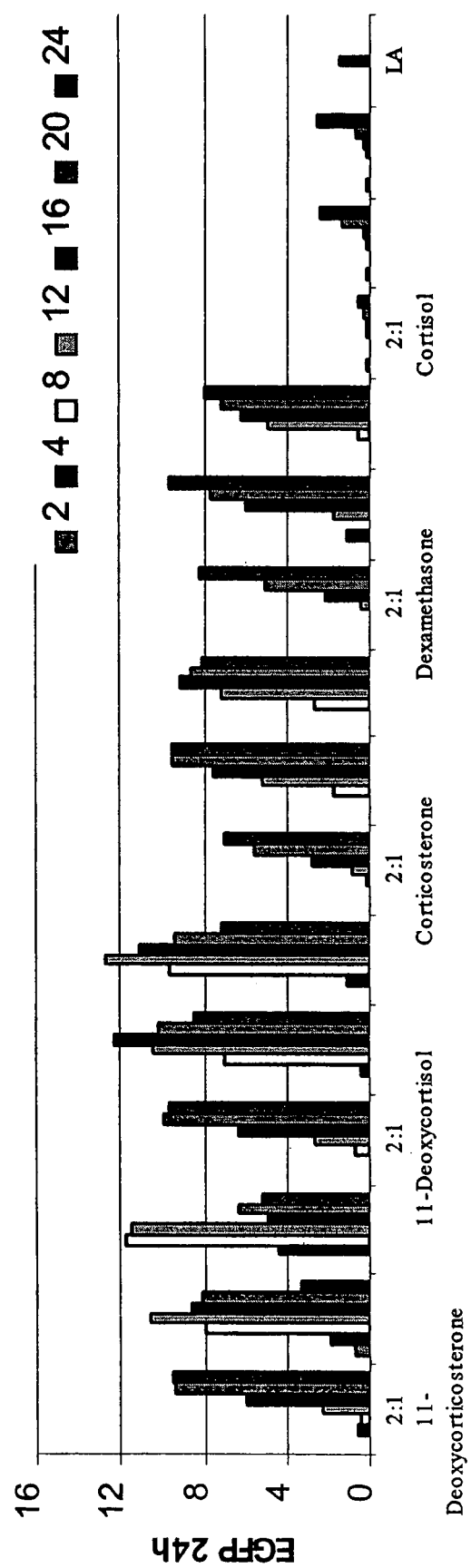

Other compounds which were coupled with spermine and tested on bovine aortic endothelial cells include 11-deoxycortisone, 11-deoxycortisol, cortisol, and corticosterone. Twenty-one formulations were tested and had varying effects on EGFP expression (see FIG. 6).

Use of Other Cationic and Hydrophobic Compounds

Based on the structural resemblance of tamoxifen (estrogen antagonist) and 4-hydroxytamoxifen to other cationic steroids (e.g., dexamethasone-spermine) or cationic cholesterol derivatives, the gene transfer activity of tamoxifen and 4-hydroxy tamoxifen was measured. To examine whether tamoxifen or 4-hydroxytamoxifen (a more active metabolite) can function as nucleic acid transfer reagents, drug was formulated with DOPE at various ratios and then mixed with DNA. GFP expression was measured in 293 cells and the results indicate that these additional steroids can be used as well in a delivery vehicle of the invention.

A number of pharmacological drugs have lipophilic and cationic groups. These compounds are in a class of molecules that can bind DNA and have gene transfer activity in the presence or absence of neutral lipids such as DOPE or cholesterol. Representative examples of other drugs that reside in the class of molecules which are cationic and lipophilic include, but is not limited to: rantidine HC, propoxyphese-N/APAP, tamoxifen, verapamil SR, triamterene w/HCTZ, trimox, acyclovir, cyclobenzaprine, methylphenidate, amitriptyline, trimethoprim/sulfa, ipratropium bromide, methotrexate, diltazem CD, norvasc, prozac and sarafem, vasotec, zestril, effexor, prinivil, imitrex, serevent, zoloft, and paxil.

These results describe a new approach to nonviral nucleic acid and drug delivery by using a novel cationic prodrug or drug vehicle. Dexamethasone, a potent glucocorticoid recognized to enhance gene delivery in vivo, was conjugated with spermine via an iminothiolane linkage. This molecule was designed to combine the gene delivery properties of the clinically relevant cationic lipids such as DC-Chol, DMRIE, DOTMA, and GL-67, with the added functionality of hydrolyzing to release pharmacologically active drug. This procedure yielded a pharmacologically active prodrug that facilitates nucleic acid and drug packaging and delivery. The use of pharmacologically active cationic steroids also allows the exploitation of anionic biopolymers such as glycosaminoglycans in the body to serve as natural occurring depots for local drug delivery.

Example 3

Pharmacological Activity of Cationic Steroids

The Materials and Methods used in the present example are now described.

Glucocorticoid Receptor Localization

The 3T3 cell line 3676 expressing green fluorescent protein (GFP)-glucocorticoid receptor chimeric protein from a tetracycline regulated promoter (Walker et al., 1999, Methods 19:386-393) was used to measure GR receptor localization into the nucleus. Cells were maintained in growth media supplemented with 100 μg/ml geneticin. The cells were incubated for 30 minutes with dexamethasone, DS, or DA ranging in concentration from 10 nM to 1000 nM, and nuclear translocation of GFP-GR was visualized at 40× using a Hamamatsu CCD camera and Leica DM IRBE fluorescent microscope.

Induction of Transcription from GRE

The levels of GRE induction using DS and its hydrolysis product DA were compared with dexamethasone using a GRE-SEAP promoter construct assay (Clontech). 293 cells were lipofected with GRE-SEAP plasmid in triplicate using 1 μg plasmid and 6 μg Lipofectamine per well in 24-well plates. After 120 minutes, the lipofection media was replaced with 500 μl of growth media, and the cells were treated with dexamethasone, DS/DOPE, or DA over a range from 1 nM to 10,000 nM. After 24 hr of induction, 50 μl aliquots of growth media were analyzed for alkaline phosphatase activity using the SEAP fluorogenic assay following the manufacturer's instructions.

The Results of the experiments described in this example are now presented.

Pharmacological Activity of Cationic Steroid

Figure 4M:
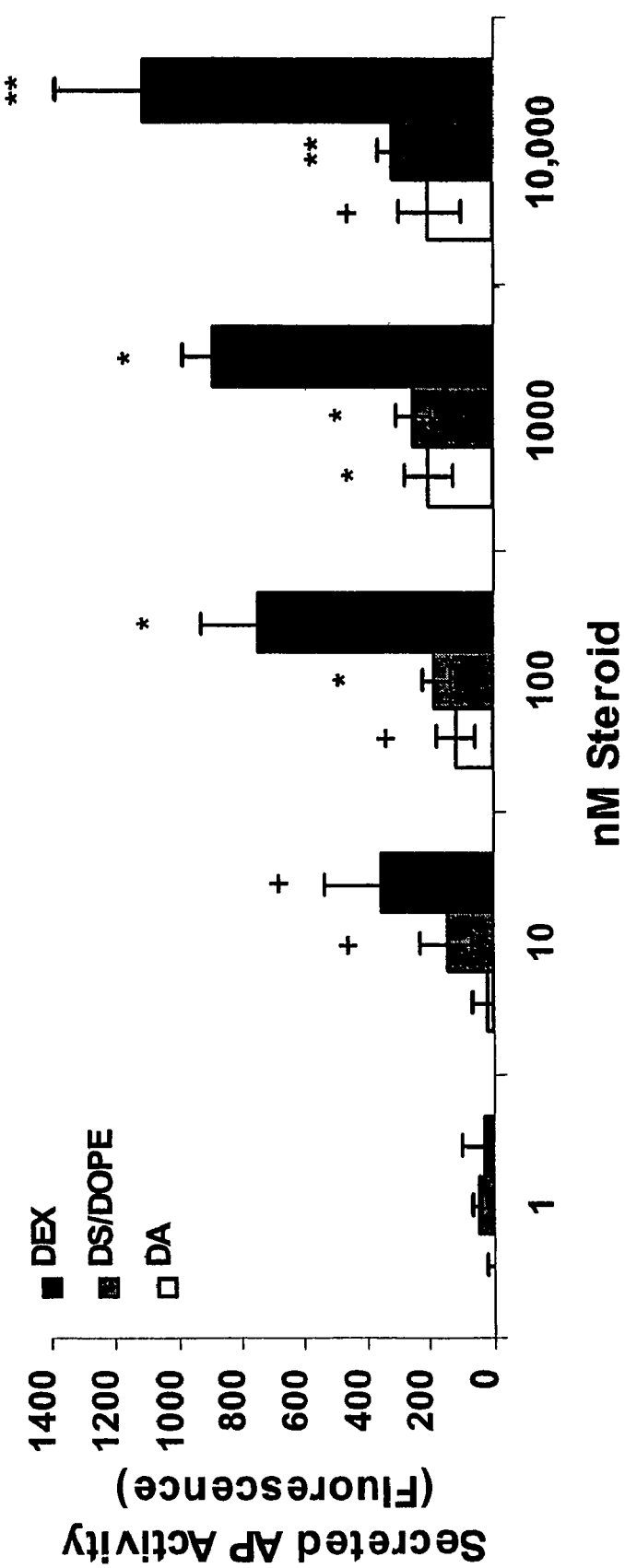

Delivery of dexamethasone, DS/DOPE, or DA at 10 to 1000 nM of steroid pharmacophore caused rapid nuclear localization of a glucocorticoid competent GFP-GR chimeric protein (FIG. 4A) stably expressed in 3T3 cells. The majority of the GFP-GR fluorescence localized within the nucleus in less than 1 hr similar to the localization induced by dexamethasone. Partial nuclear import of GFP-GR by 10 nM DS/DOPE and complete nuclear import at 100 nM, suggested that the apparent $K_D$ for this compound was approximately 10-fold higher than that of dexamethasone ($K_D$~1 nM; Ashwell et al., 2000, Ann. Rev. Immunol. 18:209-345), potentially due to reduced access to the cytosolic GR caused by endosome sequestration or association of DS with anionic elements in the cytosol. DA appeared to have similar apparent $K_D$ to that of dexamethasone since full nuclear localization was observed at 10 nM. While nuclear localization of GR is one test of glucocorticoid activity, a second test of pharmacological activity was also employed, the ability to induce gene expression from a glucocorticoid responsive promoter. Both DS and its hydrolysis product DA induced dose-dependent transcription from a GRE promoter construct (pGRE-SEAP), displaying an EC50 of ~10 to 100 nM relative to dexamethasone in 293 cells. Using Student's T Test (one tailed and two-sample unequal variance), at 100 nM concentrations, all forms of the steroid (dexamethasone, DS, or DA) induced statistically significant levels of SEAP transcription from a GRE promoter.

Example 4

Binding of a Cationic Lipid Delivery Vehicle to a Glycosaminoglycan

Glycosaminoglycans are anionic interstitial molecules which can be targeted as potential delivery sites to allow slow release of a drug, compound, or nucleic acid at a local interstitial site. There is a need in the art for a nonviral delivery vehicle which can deliver such compounds as nucleic acids or drugs to such an interstitial site, allowing them to be released in a slow release fashion. The present invention fills this need.

The Materials and Methods used in the present example are now described.

Hyaluronic Acid Release Assay

Hyaluronic acid sodium salt (Rooster Comb HA; Sigma) was diluted in PBS at 1 mg/ml to mimic an anionic glycosaminoglycan at a nominal interstitial concentration. Equal molar amounts (1 μmol) of the steroid moiety of DS, DA, or dexamethasone were added to separate HA solutions (in duplicate). The resulting mixtures were injected into 1 ml Slide-a-lyzer dialysis slides (Pierce; MWCO=10,000 Da), and dialyzed against 50 ml PBS at room temperature. The time course of steroid release from the dialysis membrane was followed by measuring the increase of absorbance of aliquots from the dialysis buffer at 240 nm ($AbS_{max}$ for dexamethasone).

The Results of the experiments described in this example are now presented.

Binding to Hyaluronic Acid in vitro

Figure 5:
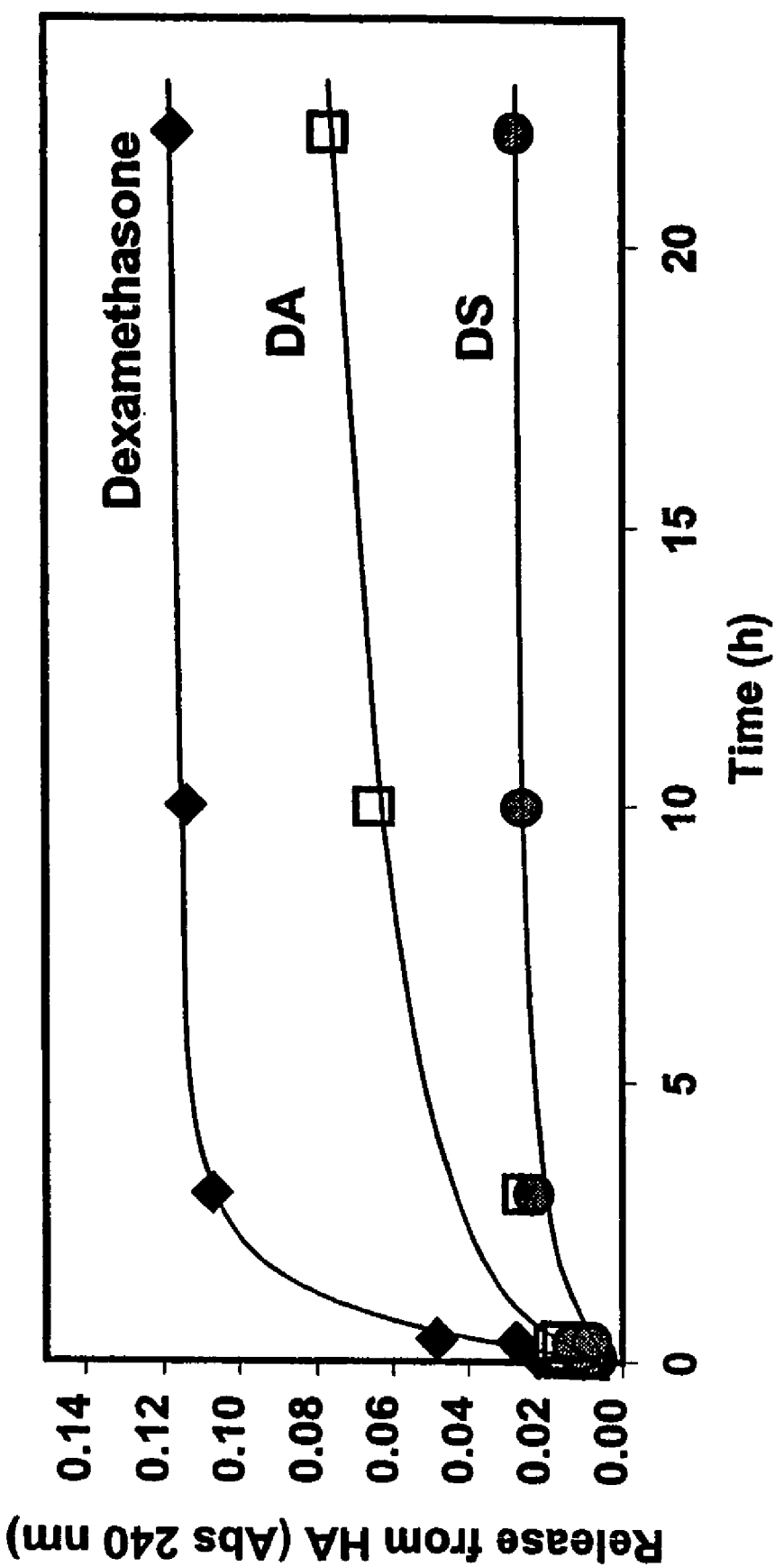
FIG. 5 graphically illustrates that dexamethasone spermine (DS) binds the glycosaminoglycan hyaluronic acid (HA). In the presence of physiological salt buffer, the release of dexamethasone from hyaluronic acid contained in a dialysis membrane was extremely rapid, while DS remained tightly bound to HA for over 24 hours, and DA had intermediate release kinetics.

Polymer-based implants are well developed for steroid delivery (as in the Norplant technology) yet the exploitation of naturally occurring anionic biopolymers as a depot is an attractive mechanism for long term, localized anti-inflammatory therapy. The results demonstrated that dexamethasone rapidly eluted from a prototypical extracellular matrix constituent hyaluronic acid (HA) in less than 5 hours. In contrast, only a small fraction of the cationic steroid DS eluted from HA in a 24 hour period, while over half of the DA eluted (FIG. 5). The half-life for dissociation from HA in PBS was calculated to be 2, 14, and 56 hr for dexamethasone, DA, and DS, respectively.

New nonviral drug delivery vehicles for nucleic acid and gene delivery and slow release prodrug applications have now been made and described herein that are easily synthesized, result in high levels of transfection or delivery when used to deliver nucleic acids, genes, drugs, or other compounds, and have their own inherent properties that add to the therapeutic potential of the delivered product.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A cationic nonviral delivery vehicle comprising a dexamethasone-spermine molecule and a lipid, wherein the spermine constituent of said dexamethasone-spermine molecule is attached through the C-21 position of the dexamethasone constituent of said dexamethasone-spermine molecule.

2. A cationic lipid nonviral delivery vehicle made by a method comprising, mixing together a steroid, a conjugating reagent, and a polyamine, wherein said conjugating reagent conjugates said polyamine through the C-21 position of said steroid via the displacement of a leaving group, purifying said conjugated steroid-polyamine molecule, and mixing said steroid-polyamine molecule with a lipid, thereby producing a cationic nonviral delivery vehicle.

3. A composition comprising a cationic nonviral delivery vehicle and a pharmaceutically acceptable carrier, said cationic nonviral delivery vehicle produced by a method comprising, mixing together a steroid, a conjugating reagent, and a polyamine, wherein said conjugating reagent conjugates said polyamine through the C-21 position of said steroid via the displacement of a leaving group, purifying said conjugated steroid-polyamine molecule, and mixing said steroid-polyamine molecule with a lipid, thereby producing a cationic nonviral delivery vehicle.

4. A kit for administering a cationic nonviral delivery vehicle, wherein said cationic nonviral delivery vehicle is made by mixing together a steroid, dimethylsulfoxide, a conjugating reagent, and a polyamine, wherein said conjugating reagent conjugates said polyamine through the C-21 position of said steroid via the displacement of a leaving group, purifying said conjugated steroid-polyamine molecule, and mixing said steroid-polyamine molecule with a lipid, said kit comprising a cationic nonviral delivery vehicle, an applicator, and an instructional material for the use thereof.

5. A kit for treating a disease or disorder in a mammal, said kit comprising a cationic lipid nonviral delivery vehicle, and an effective amount of a compound, an applicator, and an instructional material for the use thereof, wherein said compound treats said disease or disorder, further wherein said cationic nonviral delivery vehicle is made by mixing together a steroid, dimethylsulfoxide, a conjugating reagent, and a polyamine, wherein said conjugating reagent conjugates said polyamine through the C-21 position of said steroid via the displacement of a leaving group, purifying the steroid-polyamine molecule, and mixing said steroid-polyamine molecule with a lipid.

* * * * *